(12) United States Patent
Ledet

(10) Patent No.: US 9,313,623 B1
(45) Date of Patent: Apr. 12, 2016

(54) MEDICAL ANALYSIS APPLICATION AND RESPONSE SYSTEM

(71) Applicant: OPEN INVENTION NETWORK LLC, Durham, NC (US)

(72) Inventor: David Gerard Ledet, Allen, TX (US)

(73) Assignee: Open Invention Network, LLC, Durham, NC (US)

( * ) Notice: Subject to any disclaimer, the term of this patent is extended or adjusted under 35 U.S.C. 154(b) by 222 days.

(21) Appl. No.: 13/790,746

(22) Filed: Mar. 8, 2013

Related U.S. Application Data

(60) Provisional application No. 61/711,348, filed on Oct. 9, 2012.

(51) Int. Cl.
| | | |
|---|---|---|
| *G06F 15/16* | (2006.01) | |
| *G06F 19/00* | (2011.01) | |
| *H04W 4/12* | (2009.01) | |

(52) U.S. Cl.
CPC ............. *H04W 4/12* (2013.01); *G06F 19/3418* (2013.01)

(58) Field of Classification Search
CPC ....... G06Q 50/22; G06Q 50/24; G06Q 10/10; G06Q 10/109; G06F 19/322; G06F 19/326; G06F 19/3418; G06F 19/3443; G06F 19/324; G06F 19/327; G06F 19/3487; G06F 21/552; G05F 17/30489; G05F 17/30525; H04L 51/18; H04L 12/1831; H04L 67/02; H04L 69/22; G06K 9/00469; H04W 4/12
USPC ................. 709/206, 204, 203, 217, 201, 219; 705/2, 3, 7.13, 7.16, 7.18; 707/E17.022; 715/254, 751, 752, 753, 715/221, 222; 434/322, 350
See application file for complete search history.

(56) References Cited

U.S. PATENT DOCUMENTS

| | | | | |
|---|---|---|---|---|
| 5,742,905 | A * | 4/1998 | Pepe et al. .................... 455/461 |
| 6,101,532 | A * | 8/2000 | Horibe ................. G06F 3/1454 709/204 |
| 6,125,350 | A * | 9/2000 | Dirbas ............................. 705/2 |
| 8,050,937 | B1 * | 11/2011 | Henderson ....................... 705/2 |
| 2001/0042080 | A1 * | 11/2001 | Ross ............................. 707/506 |
| 2002/0105539 | A1 * | 8/2002 | Gamzon ........... G06F 17/30905 715/738 |
| 2002/0116401 | A1 * | 8/2002 | Kashito et al. ............... 707/200 |
| 2002/0138524 | A1 * | 9/2002 | Ingle et al. .................... 707/530 |
| 2003/0046109 | A1 * | 3/2003 | Uchikubo ........................ 705/2 |
| 2004/0122790 | A1 * | 6/2004 | Walker ................ G06F 19/3443 |
| 2005/0065813 | A1 * | 3/2005 | Mishelevich et al. ............. 705/2 |
| 2006/0190979 | A1 * | 8/2006 | Chwa et al. ................... 725/112 |

(Continued)

*Primary Examiner* — Alina N Boutah
(74) *Attorney, Agent, or Firm* — Haynes and Boone, LLP

(57) ABSTRACT

Disclosed is an apparatus and method of communicating with a user of a wireless device and processing message delivery. One example method of operation may include identifying a group of participants to receive a broadcast message transmitted from a wireless device, transmitting at least one broadcast message from the wireless device to a plurality of computing devices corresponding to the group of participants, receiving a plurality of response messages responsive to the at least one transmitted broadcast message, examining the plurality of response messages and extracting content of the plurality of response messages, generating a summary message based on the extracted content of the plurality of response messages, the summary message comprising portions from all of the plurality of response messages and also comprising information unique to each of the plurality of response messages, and displaying the summary message on a display interface of the wireless device.

20 Claims, 12 Drawing Sheets

(56) References Cited

U.S. PATENT DOCUMENTS

| | | | |
|---|---|---|---|
| 2007/0094188 A1* | 4/2007 | Pandya | G06F 19/345 706/45 |
| 2007/0180027 A1* | 8/2007 | Boylan | 709/204 |
| 2008/0028022 A1* | 1/2008 | Nakagawa et al. | 709/203 |
| 2008/0133274 A1* | 6/2008 | Warner | G06F 19/322 705/3 |
| 2008/0243543 A1* | 10/2008 | Jung | G06F 19/345 705/2 |
| 2008/0278740 A1* | 11/2008 | Bird et al. | 358/1.15 |
| 2009/0037545 A1* | 2/2009 | Li et al. | 709/206 |
| 2009/0192941 A1* | 7/2009 | Fournier et al. | 705/51 |
| 2010/0125565 A1* | 5/2010 | Burger et al. | 707/713 |
| 2010/0306327 A1* | 12/2010 | Shinkawa et al. | 709/206 |
| 2011/0010182 A1* | 1/2011 | Turski et al. | 705/1.1 |
| 2011/0129130 A1* | 6/2011 | Avinash et al. | 382/128 |
| 2011/0288937 A1* | 11/2011 | Manoogian, III | G06Q 30/0251 705/14.66 |
| 2012/0084096 A1* | 4/2012 | Wang | 705/2 |
| 2012/0117088 A1* | 5/2012 | Kawakami et al. | 707/749 |
| 2012/0183188 A1* | 7/2012 | Moriya | 382/128 |
| 2012/0250961 A1* | 10/2012 | Iwasaki | 382/128 |
| 2012/0278103 A1* | 11/2012 | Homchowdhury et al. | 705/3 |
| 2013/0039552 A1* | 2/2013 | Becker et al. | 382/128 |
| 2013/0096938 A1* | 4/2013 | Stueckemann et al. | 705/2 |
| 2014/0013218 A1* | 1/2014 | Lu et al. | 715/255 |
| 2014/0025394 A1* | 1/2014 | Aoki et al. | 705/2 |
| 2014/0100861 A1* | 4/2014 | Ledet | 705/2 |
| 2014/0257860 A1* | 9/2014 | Jacobus et al. | 705/3 |

\* cited by examiner

```
import java.io.BufferedReader;
import java.io.InputStreamReader;
import java.net.URL;
import java.net.URLConnection;

public class GrabHTML { public static void Connect() throws Exception{

//Set URL
  URL url = new URL("http://website here.com");
  URLConnection spoof = url.openConnection();

//Spoof the connection so we look like a web browser
  spoof.setRequestProperty( "User-Agent", "Mozilla/4.0 (compatible; MSIE 5.5; Windows NT 5.0; H010818)" );
  BufferedReader in = new BufferedReader(new InputStreamReader(spoof.getInputStream()));
  String strLine = "";

//Loop through every line in the source
  while ((strLine = in.readLine()) != null){

//Prints each line to the console
   System.out.println(strLine);
  }

System.out.println("End of page.");
 } public static void main(String[] args){
  try{
   //Calling the Connect method
   Connect();
  }catch(Exception e){

FIG. 5

MEDICAL ANALYSIS APPLICATION AND RESPONSE SYSTEM

CROSS-REFERENCE TO RELATED APPLICATIONS

This application claims priority to an earlier filed U.S. Provisional Application Ser. No. 61/711,348, entitled "System, Method and Non-Transitory Computer Readable Medium for Medical Analysis and Personalized Broadcast Message", which was filed on Oct. 9, 2012, the entire contents of which are hereby incorporated by reference.

TECHNICAL FIELD OF THE APPLICATION

This application relates to a method and apparatus of communicating with a user of a wireless device, and more particularly to controlling the reception and transmission of data messages to and from the wireless device.

BACKGROUND OF THE APPLICATION

Conventionally, users operating mobile wireless communication devices transmit and receive data messages on at a time. The users of such devices are continually increasing their usage and as a result the number of messages transmitted and received continues to increase. In order to effectively manage message flow, evaluation, and organization, the messages may be further organized, summarized and processed to provide the user with an optimal communication experience.

SUMMARY OF THE APPLICATION

One example embodiment of the present application may include a method that includes identifying a group of participants to receive a broadcast message transmitted from a wireless device. The method may also include transmitting at least one broadcast message from the wireless device to a plurality of computing devices corresponding to the group of participants, receiving a plurality of response messages responsive to the at least one transmitted broadcast message, examining the plurality of response messages and extracting content of the plurality of response messages, generating a summary message based on the extracted content of the plurality of response messages. The summary message may include portions from all of the plurality of response messages and also comprising information unique to each of the plurality of response messages, and the method may also include displaying the summary message on a display interface of the wireless device.

Another example embodiment of the present invention may include an apparatus that includes a processor configured to identify a group of participants to receive a broadcast message transmitted from a wireless device. The apparatus may also include a transmitter configured to transmit at least one broadcast message to a plurality of computing devices corresponding to the group of participants. The apparatus may also include a receiver configured to receive a plurality of response messages responsive to the at least one transmitted broadcast message. The processor is further configured to examine the plurality of response messages and extracting content of the plurality of response messages, generate a summary message based on the extracted content of the plurality of response messages, and the summary message includes portions from all of the plurality of response messages and also comprising information unique to each of the plurality of response messages. The device may also include a display configured to display the summary message.

BRIEF DESCRIPTION OF THE DRAWINGS

FIG. 2 illustrates an example software code to automatically retrieve data from a web site, according to example embodiments.

FIG. 5 illustrates yet another example user interface of broadcast message tiers, according to example embodiments.

DETAILED DESCRIPTION OF THE APPLICATION

Figure 1:
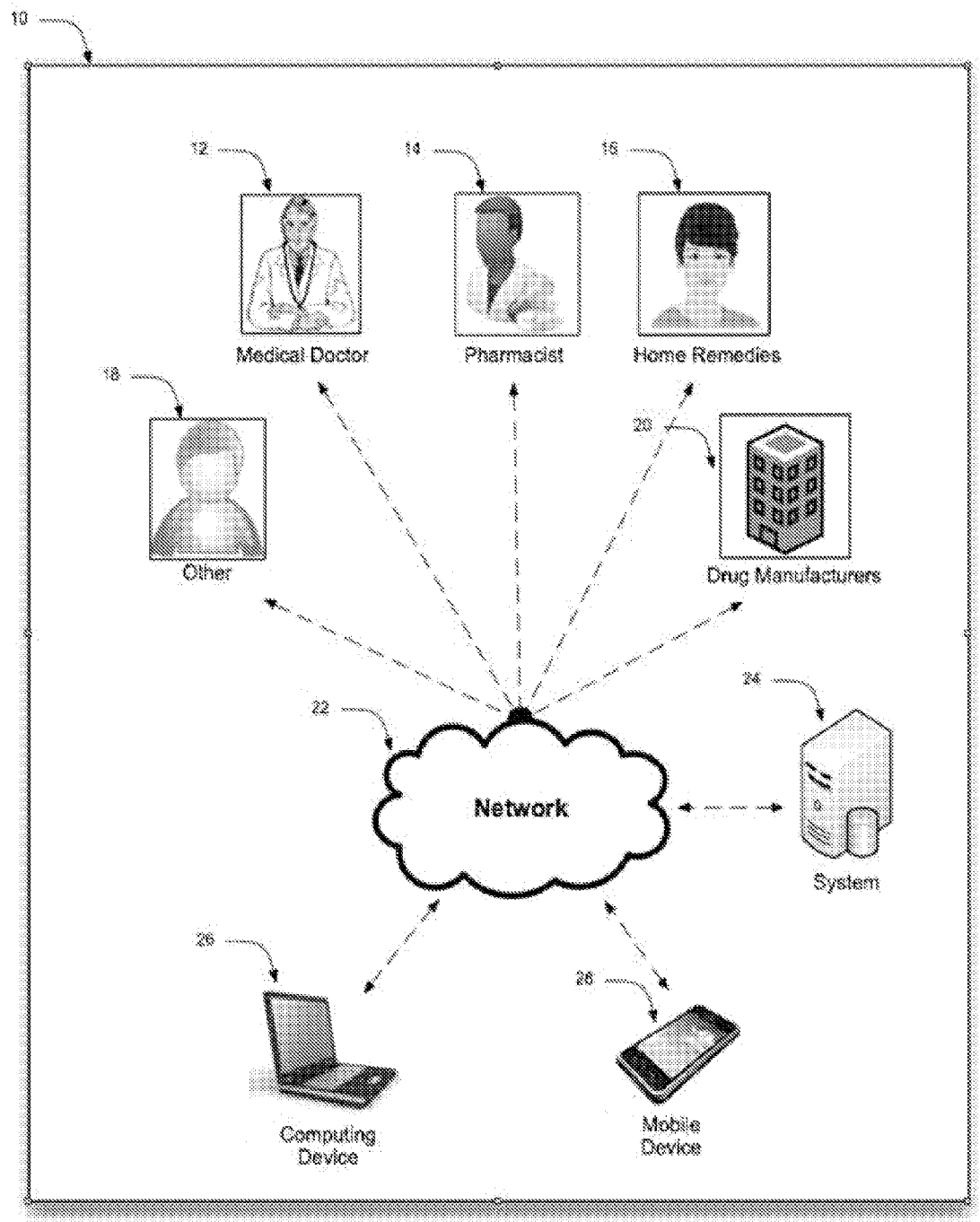
FIG. 1 illustrates an example communication network that supports wireless device communication operations, according to example embodiments.

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

Example embodiments provide a wireless user device. The device may be a computer, laptop, mobile, wireless or cellular phone, a PDA, a tablet, a client a server or any device that contains a processor and/or memory, whether that processor or memory performs a function related to an embodiment. The present application discussed throughout the disclosure may work with any device, such as a personal computer with a touch screen, a laptop with a touch screen, a personal computing tablet, a smartphone or any device with a processor, memory and a touch screen.

Example embodiments of the present application provide a user with the ability to obtain information related to a particular ailment. Such capabilities may include the tracking of non-prescribed medications, prescribed medications, generic equivalents and various home remedies. In another embodiment, the present application permits a user to transmit a personalized broadcast message (PBM) to entities within the network of the system. In another example embodiment, responses to PBMs are received by the system and a single message is sent to the user with the most popular message received or with the most concise information received based on the content of all of the messages received.

In addition to the above, the present application permits the user to be connected to one or more of the following entities: pharmacists, medical professionals, other users of the present system, and drug manufacturers. The present application also provides functionality permitting pharmacists to submit medicine related updates to ensure the users are aware of present research and new marketable products, generic equivalents, or any other information that the experts may deem helpful to users of the system. These updates are pushed to the related users to make them aware of the update(s).

FIG. 1 illustrates a network architecture 10 according to example embodiments of the present application. A user utilizing a client machine 26 or mobile device 28 may be permitted to access the system application to be downloaded from the system 24 or that presently resides on the client's device 26 and/or 28. The client device can be any of a mobile laptop device and/or a personal desktop computer 26, and/or a mobile device 28. The computing device 26 and the mobile device 28 are connected to the network 22. It should be noted that other types of devices, in addition to devices 26 and 28, might be used with the present invention. For example, a PDA, a tablet computer, a laptop, an MP3 player, a gaming device (such as a hand held system or home based system) and the like (including a P.C. or other wired device) that can also transmit and receive information could be used with the present application.

The user may interface through the client device 26/28 and connect through the network 223 to the system 24. The system can be redundant, or may be more than a single entity without deviating from the scope of the present application. The client 26, 28 and the system 24 will connect through the network 22 to one or a plurality of offsite systems 12, 14, 16, 18, 20 through the network 22.

The connected system 12 could be a medical doctor, pharmacist, home remedy specialist, drug manufacturer, general specialist or any other medical professional or otherwise expert in the related field. The connected system 14 could be a licensed pharmacist or any other medical professional or otherwise expert in the medical medicine field. The connected system 16 could be another user who has a non-medical home remedy related to the user's ailment/diagnosis and the corresponding remedy.

The connected system 18 can be another user or otherwise related system in the network that is able to offer useful information to the related ailment/diagnosis of the user. For example, registered nor non-registered nurse practitioners, an author of medical literature, a blogger of medical literature, a licensed or non-licensed chiropractor, a licensed or non-licensed physical therapist or any other entity that is able to provide useful and credible input to the user's ailment/diagnosis and related remedy.

The connected system 20 can be a user associated with the research, creation, marketing of drugs nationally or internationally. The system 24 may communicate with the connected systems (12, 14, 16, 18, 20) through the network 22. The two-way communication can occur through online messaging/chatting (either point-to-point or multicast), emails, direct communication (http posts/requests), or any of the other functionalities commonly used in systems communicating through the Internet.

The system 24 may manage other types of communication between the existing user and the connected systems. For example, video conferencing can be used to permit both the user of the present application and any of the entities in the connected systems. In addition to the video session, either party has access to the data stored in the system that is able to provide the diagnosis of the ailment or the ailment itself, the recommended treatment or any other data that was previously received by the system, the medication that the user is taking, has taken in the past or the recommended medication for the ailment/diagnosis.

The data provided by the system 24 can also include a video, lab results, the user's history (medical or non-medical), CAT scans and any other similar, relevant information. The user of the present application may interact with the system to track medications. The system retains a history of all medications that the user has taken in the past, medications that the user is presently taking. This data is stored in the system's internal database. The system also is aware of the medication that the user should be taking given a particular ailment/diagnosis. The medication(s) that that the user should be taken is stored in the internal database in the system. The system is populated with present medications that are used to treat many diagnoses. This information can be populated by any of the users of the connected systems, such as the pharmacists.

There is a benefit to using the system to track the medications as the system may have awareness of present and past ailments and diagnoses. The system of the present application permits the user to obtain varied information related to the aid of a given ailment. The information could be one or more of prescribed medications, related medications to prescribed medications, compounds, generic equivalents to prescribed medications, home remedies related to a given ailment, side effects, benefits, and/or an expected outcome. Other information may include time frames related to progress in treating the ailment, warning signs that the ailment is not abating and is digressing.

In addition to the connection with various medical professionals, the system may also retain access to medicine professionals, for example pharmacists. These medicine professionals may be identified by the application and become associated with the system as experts in the field of medicine. The system is able to connect with them when needed, and they are expected to provide their expertise as being part of the application. For example, users who take various different medications may be able to solicit a pharmacist for advice and information regarding the interaction and management of the presently administered applications prescribed by their physician. This added feature permits the system to provide a more comprehensive and complete medical scenario related to both the diagnosing of the ailment and medicine used to treat the diagnoses.

The system also retains in an internal database non-professional solutions to the aid of ailments, for example home remedies. This permits the user to obtain other remedies to the care of their ailment through the use of the present application. For example, the system obtains this data from users who submit home remedies as input to the system. In addition to obtaining the home-remedies, the system also permits the user to obtain the contact information to the person who provided the solution. The user is able to communicate with the person to discuss the home-remedy and its use and application as well as side effects.

Some users may desire to communicate with other users through the use the application of the present disclosure. The user is able to connect with other users that are using the same or similar medication or are experiencing similar symptoms or have received a similar diagnosis or advice. When a user is prescribed a medication, the system can automatically connect the user with other users who have also been prescribed that medication either presently or previously and automatically or not. The system would attempt to find other users who are most closely connected to the user (i.e., related by blood, in the same or similar geographical area, have a similar ailment, share a common age, sex, race, etc.). The system may connect both of the users or more users permitting them to communicate through video, voice, text, email, chat or any other commonly utilized methods of communication between computer systems.

For example, a user of the system may be diagnosed with elevated cholesterol. She is prescribed a generic drug, such as Simvastatin to lower the cholesterol. The system, after determining the diagnosis of the user attempts to find another user either related to her or closest to her that has the same or a similar diagnosis. Let us assume that the system found another user in the near proximity of the initial user that has the same diagnosis, but has been on the drug LIPITOR. The system can connect the two users permitting them to discuss the diagnosis and the medication used to treat the diagnosis. In addition, the system via tracking the diagnoses of other users with the same diagnosis can provide feedback as to which drug best worked in the past for that specific diagnosis providing this data to the user. Comparisons can be made by the system to permit the user to determine from actual users of the system the medication that has worked the best in the past. The data provided by the system could be data provided by the users such that they submit actual blood data that records the various levels of the cholesterol in their blood. Such data may be organized in a blog, database or other organizational format and shared by query or other searching tools.

In another example of the present application, the system can obtain other related data from users related to managing a diagnosis. For example, assuming that the user's diagnosis is high cholesterol. The system may query users about their exercise and diet. The system will also be able to provide this data to the user to educate him or her from people that he or she is related to and/or those in close proximity geographically. The data may indicate that each specific medication worked in association with exercise and diet of that particular user, and may also provide comparisons. The user may be able to determine how the drug worked in relation to exercise alone, or diet alone or a combination of any of the above based on the various data provided to the user. All of these options can be provided to the user with all of the expected benefits, side effects, time involved, etc. The user will be able to observe beforehand what the benefits may be with a combination of a particular medication and diet, or a particular medication and exercise, or a particular medication and exercise and diet.

In another example of the present application, the user is able to submit updates to the system on the progress of the ailment. For example, as the user takes the prescribed medication, changes his of here exercise regiment and/or alters his or her diet, the user can submit blood cholesterol data to the system so that the system is able to record the benefits if any are present.

The system also is able to recommend changes to the user if the ailment is not corrected after an appreciable time of the medication being administered and/or after certain life changes have been experienced. This functionality permits the user to feel more comfortable about a new or existing medication as he/she is able to communicate with another person who is actually taking that particular medication as well as research the possible changes in his/her lifestyle in combination with a particular medication.

In another example, once a user is diagnosed with a specific ailment, for example, cancer, the system pulls articles, information, and medically related data related to this type of cancer. The system uses this diagnosis word to query sites on the Internet (e.g., WebMD.com, HealthCentral.com, WrongDiagnosis.com, CNNHealth.com, etc.). The information retained is written into the internal database of the system. Likewise, the system pulls articles, information and medically related data related to the medication that the user is prescribed and/or presently taking.

FIG. 2 illustrates an example of software code that that retrieves an HTML source from a given uniform resource location (URL) web link. Referring to FIG. 2, one skilled in present programming techniques could use the pseudo code to obtain text from a specific web site, and then parse the text and recursively identify data sources using further URLs obtained from the text. A spoofing algorithm is necessary to fool the web site so that the connection appears as a web browser to the web page. In the pseudo code, the text of the web site is printed to the terminal, which would be altered to be written to the system's database. The system would then be able to automatically obtain specific information from various web sites pertaining to a particular diagnosis that are then written to the internal database and characterized accordingly.

The system may also seek access to treatments of the specific diagnosis and other trials pertaining to the diagnosis of the user. Once this medical data is obtained, the system utilizes metrics to determine a recommendation for the user based on their condition and the results of the findings in the articles obtained from the research performed. In operation, the system connects with the computer servers and related infrastructure of a manufacturer of the medicines. Through the use of the application, the user is able to connect with the manufacturer of the medicine they are presently taking or have been prescribed in an effort to receive education information, updates, recalls, special information, related medicine updates, etc. The communication between the user and the manufacturer can be via by video, voice, text, email, chat or any other method of communication from one computing device of the manufacturer to another computing device of the user.

The user of the present application is able to submit inquiries about a particular medication. The system receives these inquiries and then routes these inquiries to licensed pharmacists that have opted into the system of the present application. The system then permits the user and the licensed pharmacists to communicate by video, voice, text, email, chat or any other method of communication. The user would benefit by knowing that the information he/she is receiving is from a licensed pharmacist. The pharmacists may set up a profile and be part of a pool of pharmacists prepared to receive the inquiries for hire based on geographical location, skill set, etc., with respect to the user.

Pharmacist awareness flags may be identified and maintained throughout the application. For example, the licensed pharmacists are able to provide new items of interest in the medicine field. These items of interest may include new medicine interactions, new possible side effects of medicine, etc. These items of interest may come for various sources, for example, published medical journals that pharmacists regularly use and know. Through the use of the application, the pharmacists are provided with the ability to submit these new medicine-related realities into the system. These submissions are internally referenced as "Awareness Flags". The awareness flags are then delivered to any user that is presently taking that medication.

Figure 3:
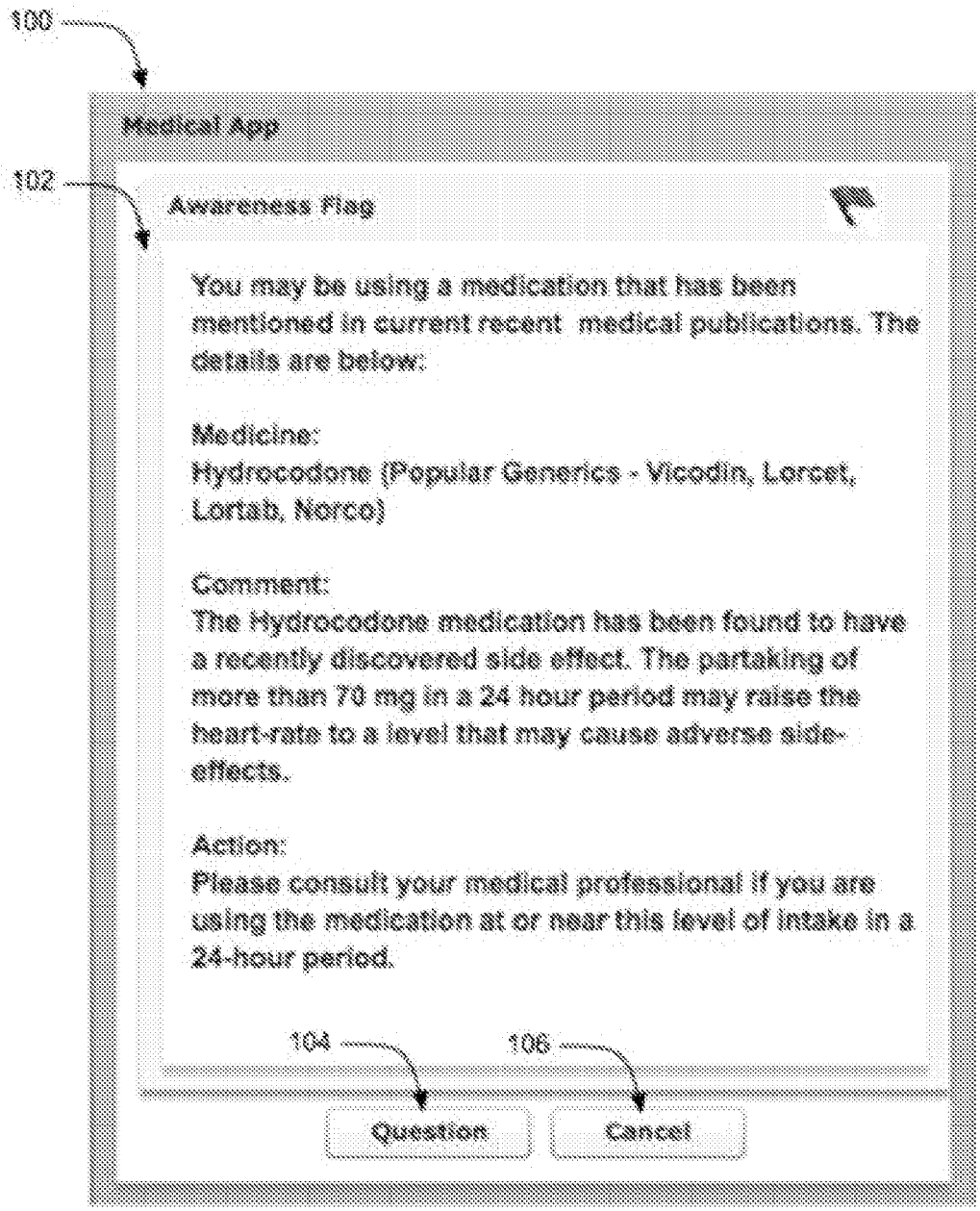
FIG. 3 illustrates an example user interface illustration of an application interface operated by the wireless device, according to example embodiments.

FIG. 3 illustrates an example GUI depiction of an awareness flag. FIG. 3 is a snapshot of an example of the GUI of the present application. The GUI representation 100 illustrates a possible awareness flag that is generated by the system. The window has three areas, the message area 102, and two buttons for interaction by the user 104 and 106. The message area contains the data of the message. The question button 104 permits the user to submit a message to the system. When the question button 104 is pressed, a window is displayed (not depicted) that permits the user to type a message. This message is forwarded to the system, and then forwarded to the creator of the awareness flag. When the cancel button 106 is pressed the window is removed. This configuration permits the users of the present application to have up-to-date awareness of recent findings related to medication without having to educate themselves from other data sources. The system automatically informs the user of the new findings as they are updated via the linked sources established with the system.

The system of the present application also connects to entities that are aware of present medical developments including the latest research, medical trials, etc. These entities are able to submit updates to the system, which notifies the affected users making them aware of present changes in the availability of medication. For example, when a medicine is recently available under a generic name. The system then updates the users of that particular medicine making them aware of changes that may permit them to identify the generic equivalent, or another medication. The system looks globally for solutions as many countries have hospitals, facilities, doctors and drugs that the U.S. medicine references do not access or that the FDA has not yet approved. Many countries have home remedies or personal remedies that are not known in the U.S. Also, the system will translate the information (text, speech, etc.) so the user can understand the information in their own language.

Also, the system through the communication with these entities may alert the user that new research has been published that specifies alternative medicine is available that may be substituted for a given medicine or prescription regiment. This permits the user to be aware of changes in the marketing of medicine without having to perform their own research. Also, the system through the communication with these entities may notify the user that homemade remedies or other non-medicine alternatives are discovered that alleviate the need for certain medications. These remedies may include compounds, ointments, etc.

The system of the present application will inform the user of possible side effects of medication and transmit a notification to the user. The system obtains this medicine related information by using the same functionality. For example, a side effect of a medication may be diarrhea so the user is requested to take another drug that minimizes that particular side effect. Or the system may inform the user to be sure to drink 'X' number of glasses of water before and/or after the medication. The system may inform the user of one or both of the above recommendations or provide other recommendations that are not commonly found on the prescription label of a pharmaceutical drug.

The system of the present application may transmit a notification to the user at a pre-determined time and may request the user to submit additional data to help determine the side effect of a particular medication. This notification may be user to request the user to inquire about taking another medication or perform another action. When the system is aware of a user taking a new medication, a request will be sent to the user to determine whether the user is experiencing any side effects. This functionality permits the user of the present application to be made aware of the possible side effects of medicine he/she is taking without having to perform research. The notification will request the user to submit data that reflects the medical condition to determine if any side effects of the medication are known and should be provided to the user.

Figure 4:
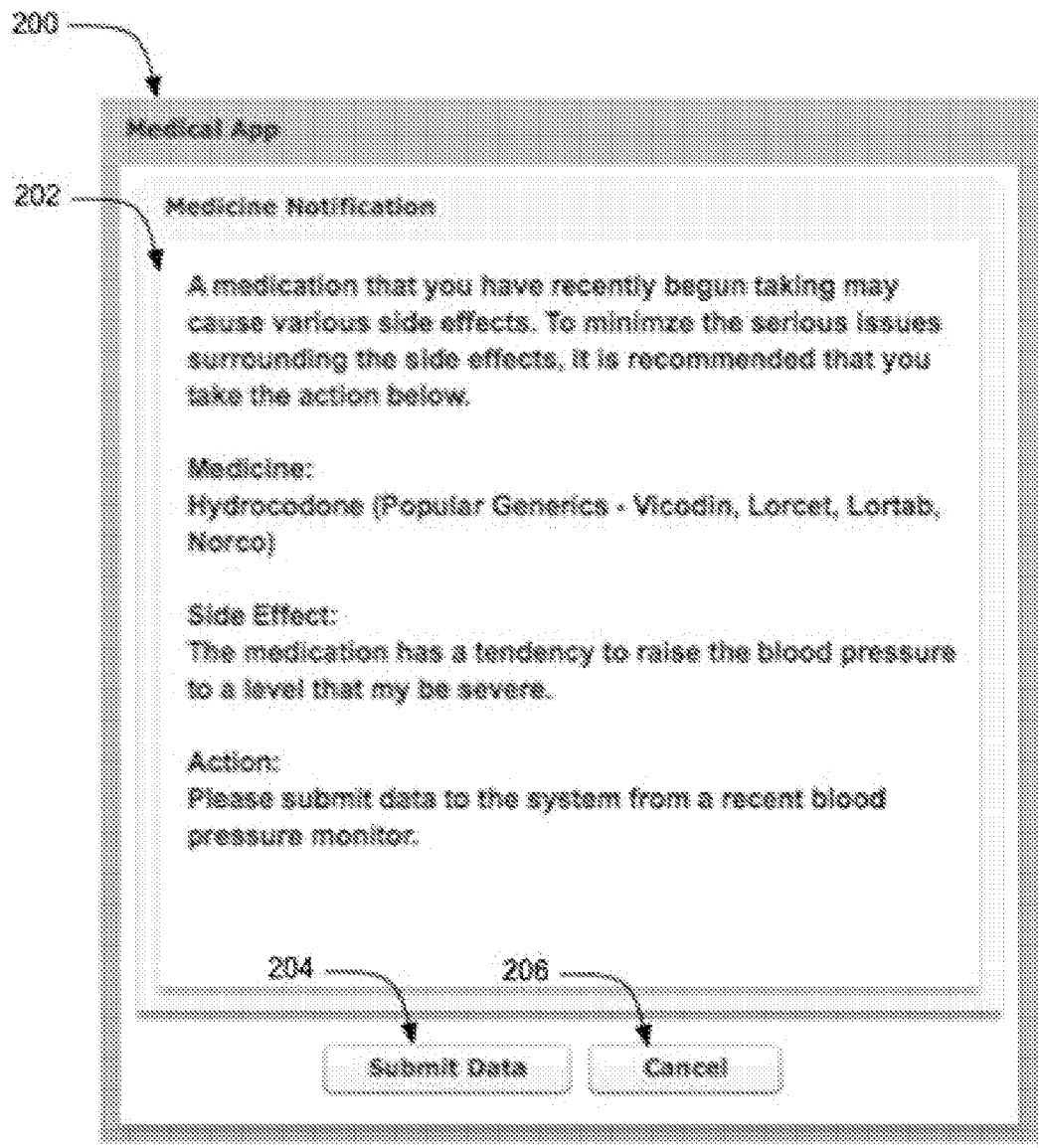
FIG. 4 illustrates another user interface illustration of an application interface operated by the wireless device, according to example embodiments.

FIG. 4 illustrates another example GUI for the user to access medicine information, according to example embodiments. Referring to FIG. 4, the GUI representation 200 illustrates a possible notification that is generated by the system of the present application. For example, the window has three main areas, including the message area 202, and two buttons for interaction by the user 204 and 206. The message area contains the data of the message. The submit data button 204 permits the user to submit data to the system. When the submit data button 204 is selected, a window is displayed (not depicted) that permits the user to submit data from a connected medical device communicably coupled to the user's device, or any other medical device used to capture medically related data. This message is forwarded to the system and treated as input regarding the ailment and/or diagnosis of the user. The system processes the data as other input from the user. When the cancel button 206 is selected, then the window is removed.

The system may transmit an inquiry to the user to submit data regarding heart rate, blood data, oxygen levels, etc. The user would utilize connected medical devices to obtain the data that is then utilized to check if the data is within acceptable levels for optimal health. The system would look for side effects of the medication prescribed and understand what data to request and be aware of possible side effects of the user's medication. In the event that the user does not comply within a certain period of time the system transmits the action again and the user can cancel it at any time if they do not want to perform the action.

According to another example embodiment of the present application, certain broadcast messages may be transmitted from the user device to various different recipients. The ability to transmit personalized broadcast messages (PBMs) to other entities (i.e., individuals, computers, etc.) in the system provides communication via one or more protocols such as email, voice, voice mail, short message service (SMS), audio and/or video on a user's device, for example, a mobile wireless device. One of the functions enables the transmitting of PBMs to other entities in the system and another function provides for the analysis of responses which may occur automatically. This may provide fewer responses than the number of received messages such as a single response depending on the results of the analysis.

The broadcast SMS messages may be transmitted via a SMS Gateway. The SMS gateway may operate according to a software program that is downloaded to a user's device. The recipients may be part of a subscription list and may use the computer to initiate the broadcast SMS message. The application on the user's device uses the subscription list to sequentially transmit multiple SMS messages through the SMS gateway. Additionally, example embodiments may transmit PBMs and reply with an automatic analysis of responses to PBMs and provide a single response or summary according to the results of the analysis.

According to one example, a personalized broadcast message (PBM) may transmit data via one or more protocols such as short message service (SMS), audio and/or video on a user's device such as a PC or a mobile device that can include a mobile phone, tablet computer, laptop, PDA and any type of mobile device that includes a memory and processor. By example only, a SMS or text message is sent as a PBM and is delivered to one or more of the user's recipient(s) that may be selected by the instant application or may already be a part of a group of intended recipients. When the user transmits a broadcast message via the application, instead of all recipients receiving the same message, each recipient may be treated differently. Some recipients may receive a simple text message and some may receive additional data that is automatically sent by the application. The recipients that have a closer relationship with the user of the application may receive more pertinent or personalized data from the user reflecting their closer relationship. The various tiers of users or groups of users may be designated to receive certain messages while others may receive other messages.

According to one example, the ANDROID® operating system, for example, supports transmitting SMS text messages. To transmit a SMS text message, the 'SmsManager' class can be used. Unlike other classes, this class does not have to be directly instantiated; instead the getDefault( ) static method to obtain a 'SmsManager' object is called. The 'transmitTextMessage' method transmits the SMS message via the 'PendingIntent' object. The 'PendingIntent' object is used to identify a target to invoke later. For example, after transmitting the text message, you can use a 'PendingIntent' object to display another activity. In this case, the 'PendingIntent' object is simply pointing to the same activity (SMS.java), so when the SMS is sent then nothing will happen.

The process uses a 'PendingIntent' object (sentPI) to monitor the transmitting process. When an SMS message is sent, the first broadcast receiver's 'onReceive' event executes. This is where a status check of the transmitting process is performed. The second 'PendingIntent' object (deliveredPI) monitors the delivery. The second broadcast receiver's 'onReceiveevent' will execute when an SMS is delivered successfully.

According to another embodiment of the present application, the application may automatically perform analysis of the responses and distill those responses into certain data such as questions, statements, and related message etc., that is/are presented to the user to summarize relevant portions of data received in all of the responses and/or combines the most important data into a single question, statement, etc. The user can then transmit another broadcast message without having to read through all of the individual responses, still knowing that the most important data in the responses have been addressed in the sent broadcast message.

The application may reside on the user's wireless device or smartphone, but can also reside on a user's desktop computer, a personal digital assistant (PDA), tablet computer, or any other device containing a processor, memory, and an operating system. If the application resides on a mobile device, the application is downloaded through a platform such as an application store or market residing on the device or accessed via the device. Upon installation and/or initialization, the user has the option of establishing tiers of recipients to organize which recipients receive which levels of types of broadcast information. A tier of recipients permits the application to transmit different data to the different tiers of recipients. One example may be family and work, as two separate tiers receiving different types of broadcast information.

The user is also able set a configuration table where the following can be selected/configured: configuration component type, such as yes or no, checkbox, number indicator, etc., and a default setting, such as on, off, 1, 2, 3, 10, etc. Examples of configurations may include: transmit a picture to Tier-2 recipients, transmit video to Tier-1 recipients, automatically determine recipients in tiers, number of contacts per tier, time to analyze responses, time for second analysis, and number of questions to display.

The user has the option to configure various elements of the application. This configuration component can be displayed to the user upon the first initialization of the application. Also, a menu can be provided to the user that at any time, access is provided to alter the configuration elements.

According to one example, the element: "transmit a picture to tier-2 recipients" is a checkbox that is initially unchecked. If the user checks the checkbox when transmitting a PBM, a picture (jpg, gif, etc.), if available, will be sent to tier-2 recipients along with the broadcast text message. The element: "automatically determine recipients in tiers" is a checkbox that is initially unchecked. If the user checks the checkbox, the application first displays a warning message to the user that the contact in all tiers will be removed. The user has an option to dismiss the warning and no changes are taken by pressing the "Cancel" button. If the user presses the "OK" button, all contacts in all of the tiers are removed. The application, utilizing the operating system of the particular mobile device, accesses the text message history and sorts the list in a descending order or can determine the order of contacts based on the number of text messages and the related content in the history. The application then utilizes the configuration element number of contacts per tier" value to place that number of contacts into each tier. For example, if the value of the "number of contacts per tier" is "3", then the first three contacts in the descending contact list is placed into the tier-1 list. Then the next number of contacts is placed into tier-2, followed by the next number of contacts placed into tier-3.

In another example, the element: "transmit video to tier-1 recipients" is a checkbox that is initially unchecked. If the user checks the checkbox, when transmitting a PBM, either prerecorded video or live video from the user's mobile device, if available, is sent to the tier-1 recipients. The element: "number of contacts per tier" is a numerical input that initially has the value of "3". This element configures the number of contacts in each of the recipient tiers. If the user enters a numerical value into this field, the number of recipients will be reflected in each tier. If the user decreases the number, a warning message is sent to the user reflecting that contact will be removed to account for the number of contacts specified.

The element: "time to analyze responses (minutes)" is a numerical input that initially has the value of "10". This element indicates the amount of minutes the application waits before beginning to analyze the responses. A timer is started when a PBM message is sent from the application. The timer expires when the number of minutes has passed that is in the configured element. The element: "time for second analysis (minutes)" is a numerical input that initially has the value of "10". This element indicates the amount of minutes the application waits after the initial timeout expires to analyze the responses again. The timer is started when the first timer expires. The timer expires when the number of minutes has passed that is in the configured element. The element: "number of questions to display" is numerical input that initially has the value of "2". This element indicates the number of questions to display to the user once analysis of the responses from the recipients has been analyzed. One example range of acceptable values is between 1 and 10 but can include a greater number.

The user may place the recipients into different levels, subsequently referred to as tiers, according to his/her relationship with each recipient, or the application may determine the relationship based on the frequency and type of correspondence. The user has the option in the configuration section of the application to determine if the tiers will be setup automatically. When the application is tasked with determining the tiers, the application examines the SMS history on the user's device. Each of the contacts in the users contact list stores the number of SMS messages sent. The application sorts the list in a descending order to determine the contacts that were previously sent the most SMS messages. The configuration element entitled: "number of contacts per tier" is used to determine the number of contacts to place in each tier. This configuration element defaults to "3" if the user has not selected a value. In this example, the recipients that the user has sent the most text messages in the past will be placed in the top tiers automatically, with the assumption that they are the closest recipients to the user.

Other methods can be used to automatically determine the recipients in the tiers if the user has configured to permit the application to determine the recipients in the various different tiers. For example, the application can attempt to match the recipients in the text history to the recipients that the user has emailed. This is performed through analysis of the previous emails in the user's mobile device or other computer devices. This additional analysis will assist the application in further determining the relationship of the recipients to the user.

Assuming that the user not selected to have the application automatically determine the recipients in the tiers, the user can configure the recipients according to the relationship of the recipient to the user of the application. For example, the pharmacists and/or doctors and/or medical professionals that are closest to the user would be placed in tier-1. The next group of recipients would be placed in tier-2 and may include those that are possibly in the user's geographical location (i.e., same city). Another group, tier-3, may include all other pharmacists and/or doctors and/or medical professionals. Various tiers can be setup according to the user's various relationships, such as business contacts, social network, family, or along any other relationship.

FIG. 5 illustrates an example broadcast message tier GUI, according to example embodiments. Referring to FIG. 5, the various tiers (i.e., tier 1, tier 2) that are setup on a user's mobile device may include contacts that are included in the tiers, and which can be inserted by showing the user recipients in the contact list. When the "+" symbol is selected, the tier members may be expanded to include a list. In operation, the tiers may be setup automatically depending on various recipient selection criteria, such as geographical location of recipient as compared to the user, relationship, frequency of messages exchanged, family name, SMS message frequency, SMS message content, etc. Or, the user may manually select a contact, and that contact would be placed inside the respective tier.

If the number of contacts in any tier has increased beyond the configuration element, such as "number of recipients per tier", a warning message may be presented to the user reflecting the number of tier members is close to being exceeded. The user has the option to dismiss the change by selecting the "Cancel" button, or proceed with the addition by pressing the "OK" button. Alternatively, for example, the user can remove a contact from a tier by holding down the contact and a sub-menu may be displayed as the list enters into an edit mode. In one example, the user can move recipients between tiers by pressing a contact in the list, holding it down, and then the application changes the display of the contact, making it appear lifted. Next, as the user then moves the finger on a mobile device or otherwise a pointing device, the contact moves along with the movement of the finger or pointing device.

As the user moves into another location, the existing contacts move to make room for the new addition. As the user lifts the finger or pointing device, the contact is "dropped" into the slot that has been made for the new user. If the number of contacts in any tier has increased beyond the configuration element: "number of recipients per tier", a warning message may be presented to the user identifying the maximum user concern. The user may have the option to dismiss the change by pressing the "Cancel" button, or proceed with the addition by pressing the "Ok" button.

The user also has the option to select media on the mobile device that is sent to tier-1 recipients when the PBM is broadcasted to the various users. When transmitting a broadcast message to the recipients through the application, the user is queried as to whether live video is to be broadcast, or other data content. When a user transmits out a personalized broadcast message (PBM) to all selected recipients via the application of the present invention, instead of simply transmitting the message to all recipients, those in tier-2 would receive more personal data, and those in tier-1 would receive even more additional data, as these recipients are the most intimate/privileged/relevant with the user or the user's intended message content. Each group of recipients would receive data from the user reflecting their relationship with the user.

When the user transmits a PBM to all selected recipients, the content that is delivered to the recipients may vary according to the particular tier that the recipient is placed. For instance, those recipients in tier-3 would be simply sent a sub-set of the total original message that the user sent, for example, only a SMS message. Those in tier-2 would also receive the SMS message, but in addition would receive additional information such as a .jpg data file or photo that has been previously selected by the user or by the application. Those participants in tier-1 would receive the SMS message, the photo previously sent, plus live video from the user's mobile device. For example, the contacts in tier-3 would receive the simple text message. Those contacts in tier-2 would receive the text message and an image, for example a picture of the medication. Those participants in tier-1 would receive the text message, the image, as well as a live video and the user would be able to transmit a video to the medical professional. The configuration area of the application permits the user to configure the picture that is sent to a tier-2 recipient by selecting the checkbox entitled: "transmit a picture to tier-2 recipients."

The configuration area of the application also permits the user to configure whether or not a live video is sent to the recipients by selecting the checkbox entitled: "transmit video to tier-1 recipients." When transmitting the original PBM to recipients in any tier, the system forwards the message to entities that are part of the network. Referring to FIG. 1, the system 24 receives the original PBM from the user via either a computing device 26 or a mobile device 28 through the network 22. This message is processed and either the original message or a revised message is sent to one of the other entities in the system 12, 14, 16, 18 or 20 through the network 22.

When the user requests for live video to be sent, after the user transmits the broadcast SMS message, the mobile or other computing device is then switched to the video component where the user has the option to begin recording. In the ANDROID mobile operating system, the 'MediaRecorder' class contains procedures to configure the video recorder. The functions below are utilized to record video in the ANDROID operating system and may be used by the present application: setVideoSource( ); this sets the video source (i.e. camera or default) to be used for recording; setOutputFormat( ); this sets the format of the output file produced during recording; setVideoEncoder; this sets the video encoder to be used for recording; setOutputFile( ): This sets the path of the output file; setPreviewDisplay( ): Sets a Surface to show a preview of recorded media (video); prepare( ): Prepares the recorder to begin capturing and encoding data; start( ): Begins capturing and encoding data to the file specified withsetOutputFile( ). In operation, the user selects the record button and the video begins to record, storing the video file on either the mobile device's internal memory or an external memory depending on the configuration of the mobile device. The live video is transmitted to the remote recipients included in the tier-1.

In another embodiment of the present invention, location services are utilized to permit broadcast messages to automatically be sent to recipients of the user. This permits recipients in the predefined tiers to receive specific data from the user depending on the user's geographic location and/or the recipient's geographic location. Before the application automatically transmits out a broadcast message, the user is first notified and must verify that message PBM should be sent. For example, a PBM may be automatically sent to the recipients when the user is not within his/her "usual" area. This "usual" area can be the user's hometown, or any other geographic location defined in the application by the user. The application can also transmit the PBM to recipients in the tiers when the user enters a geographic location. In another example of the present application, broadcast messages can be automatically sent according to the user's time of day, speed of travel (i.e., when driving, not driving, etc.), present weather conditions, etc.

Figure 6:
FIG. 6 illustrates an example signaling diagram of a user input and response system, according to example embodiments.

FIG. 6 illustrates a signaling diagram of a message flow transmitting a PBM. Referring to FIG. 6, a message flow is depicted where the application resides on the user's mobile device 602. A recipient in tier-1 206, a recipient in tier-2 608, and a recipient in tier-3 610 represent the recipients of the user's PBM(s). The user's mobile device 602 is connected to the recipients in the tiers 606, 608 and 610 by a data network depicted by the Internet cloud 604. The user initiates the process by entering the text message in the application 612. The text message is sent 614 to the Internet 604 with the destination of the recipients in tier-3 610. The Internet 604 forwards the text message 616 to the recipients in tier-3 610.

A check operation is performed by the application to determine if the user is configured to transmit additional data, in this case a picture 618. If the application determines that a picture should be sent, the original text message and the picture is sent 620 to the Internet 604, and forwarded to the recipients 622 of tier-2 608. The application determines if even more additional data should be sent 624 depending on the message type, the tier level of the recipient(s), etc., and in this case transmits the original text message, the picture, and the video data 626 to the Internet 604, and then the message 628 is forwarded to the recipients in tier-1 628.

Figure 7:
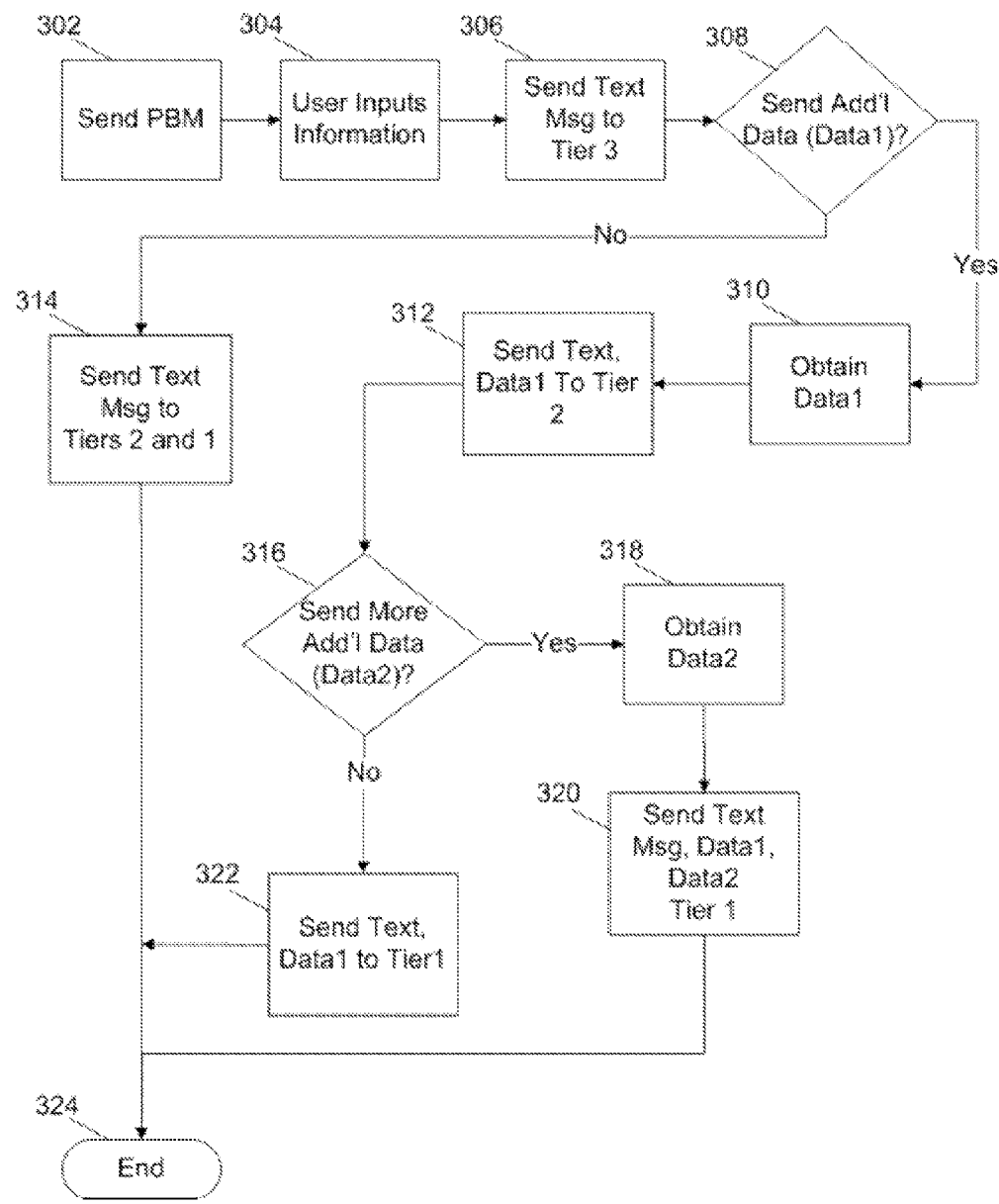
FIG. 7 illustrates an example flow diagram of a user message transfer, according to example embodiments.

FIG. 7 further describes the process of transmitting a PBM message. In FIG. 7, the user utilizes the application to initiate the PBM 302 by entering the text to be included in the PBM and selecting the recipients in the tiers 304. The text message is sent to the recipients in tier-3 306. These recipients are the ones that are the least intimate with the user, and thus they receive the text message in the PBM only and no other data. The application then determines if the user requests to transmit any additional messages in the PBM 308 (i.e., subsequent PBMs, the same PBM, etc.).

If the user is not configured to transmit additional data in the PBM, the original text message will be sent to the recipients in tier-2 and tier-1 314, and the process ends 324. If the user is configured to transmit additional data with the PBM, the additional data ('Data 1') is obtained from the user device 310. This can include an image, a data file, a video file, or any other data preconfigured by the user. The original text message and the additional data is then sent to the recipients in tier-2 312.

The application then determines if the user has configured even more additional data to be included in the PBM 316. Such additional data can be an image file, a data file, a video file, or any other data configured by the user prior to attempting to transmit the additional data to the recipients in the various tiers. If the user has not configured even more additional data to be sent in the PBM, the original text message and the additional data ('Data 1') is sent to the recipients in tier-1 322. If the user has configured even more additional data to be sent in the PBM, the data is obtained from the user 318, and the original text message, the additional data ('Data 1') and the even more additional data ('Data 2') is transmitted to the recipients in tier-1 and the process ends 324. Another example may provide additional data that is transmitted, such as a picture, and even more additional data that is transmitted, such as a video. The video can be either a prerecorded video file or live video from the user's mobile device.

Figure 8:
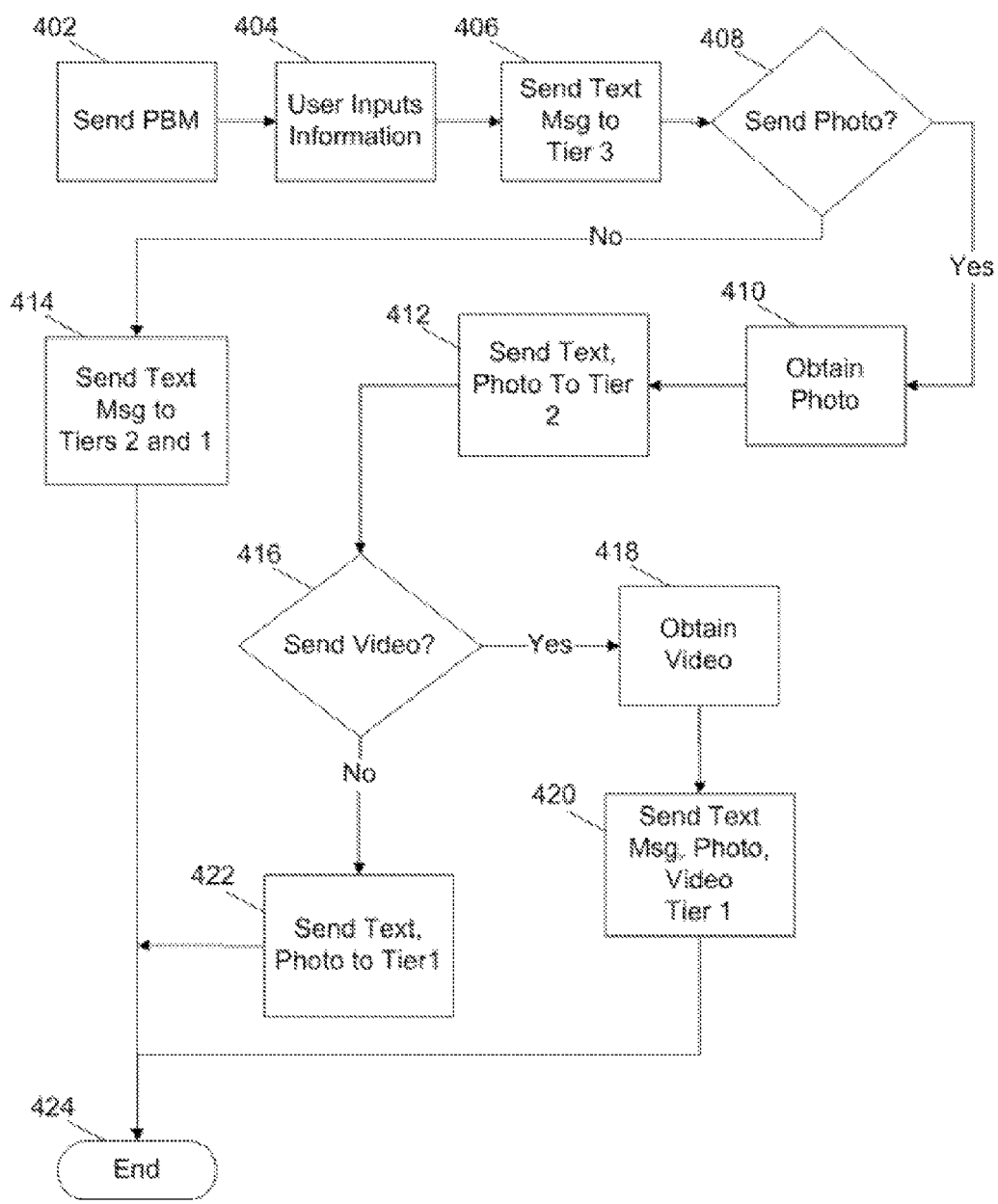
FIG. 8 illustrates another example flow diagram of a user message transfer, according to example embodiments.

FIG. 8 illustrates an example flowchart of transmitting a PBM. Referring to FIG. 8, the user may select to transmit a broadcast message through the application 402. The user first is presented with a texting screen where the text to be broadcast is composed 404. The user enters the broadcast message and presses a "Continue" button. The application transmits the original text message of the PBM to the recipients of tier-3 406. The application then identifies the value of the configuration element: "transmit a picture to tier-2 recipients" 408.

If the configuration of the element is not checked, the application then transmits the broadcast text message to the recipients in tier-2 and tier-1 414, and the process ends 424. If the configuration of the element is checked, the user is presented with a window 410 where a picture can be selected from the following choices: 'take a new picture', and 'select a picture from the gallery'. If the first option is selected, the mobile device switches to the camera component of the camera where the user can take a new picture. The picture is then utilized in the application. If the user selects the second option, the user is presented with a gallery of photos existing on the mobile device where the user can select a picture.

Once the picture of image file is selected from either of the two choices noted above, the application transmits the original text message and the image file to the recipients in tier-2 412. The application determines if a video file is configured to be transmitted to the recipients in the PBM by referencing the configuration element: "transmit video to tier-1 recipients" 416. If the configuration element has not been selected, the application transmits the original text message of the PBM and the image file to recipients in tier-1 422 and the PBM operation ends 424. If the configuration element has been selected, the video data is obtained from the user 418 and the application transmits the original text message of the PBM, the image file, and the video data to the recipients in tier-1 420. The PBM operation then ends 424.

In another example embodiment, the application analyzes the responses of the recipients in response to a transmitted broadcast message, which permits the functionality of the application to be dynamic. A timer is then initiated when a PBM message is transmitted from the application. The timer expires when the predefined number of minutes has passed that is set in the configuration element "time to analyze responses ('x' minutes)". Upon expiration of the timer, the application analyzes all of the responses received from a broadcast message and automatically determines the most important response to pose to the user according to analysis of the responses. The analysis may be based on keywords, nouns, unique terms, audit information, etc., that is parsed from the message content of various responses.

In another embodiment, the application may combine the most important questions into a single message (i.e., summary message), and presents the single message to the user for approval. In another embodiment, analysis of the responses to the broadcast message occurs in a first period of time, for example 10, 20, 30 60 seconds, and then in a second period of time, such as 2 minutes or 1 minute past the first minute (i.e., a new summary may be generated every minute for three minutes). After the first analysis, a summary message is transmitted to the user. After the second analysis, another summary message is sent to the user if different from the first message.

Example embodiments may utilize natural language processing (NLP) and/or text parsing to analyze the received responses to a PBM. A NLP is a processing engine/algorithm that conducts processing interactions between a computer and spoken voice input. Utilizing NLP, it is possible to determine the number of instances of a word together with some context in a given group of texts. Utilizing the PYTHON computing language, the context of the word in the text may be identified along with grouping of similar uses of a word, and a location to determine where in the sentence the word appeared.

With reference to FIG. 1, the system of the present application 24 utilizes NLP to analyze the responses received from the recipients of the PBM 12, 14, 16, 18 and 20 through the network 22. Each response is parsed and analyzed to determine the meaning of the response, and compared to other responses to determine the most appropriate single response to the transmitter of the initial PBM by the system 24. The most appropriate response is sent to the initial transmitter of the PBM 26, 28 through the network 22.

Figure 9:
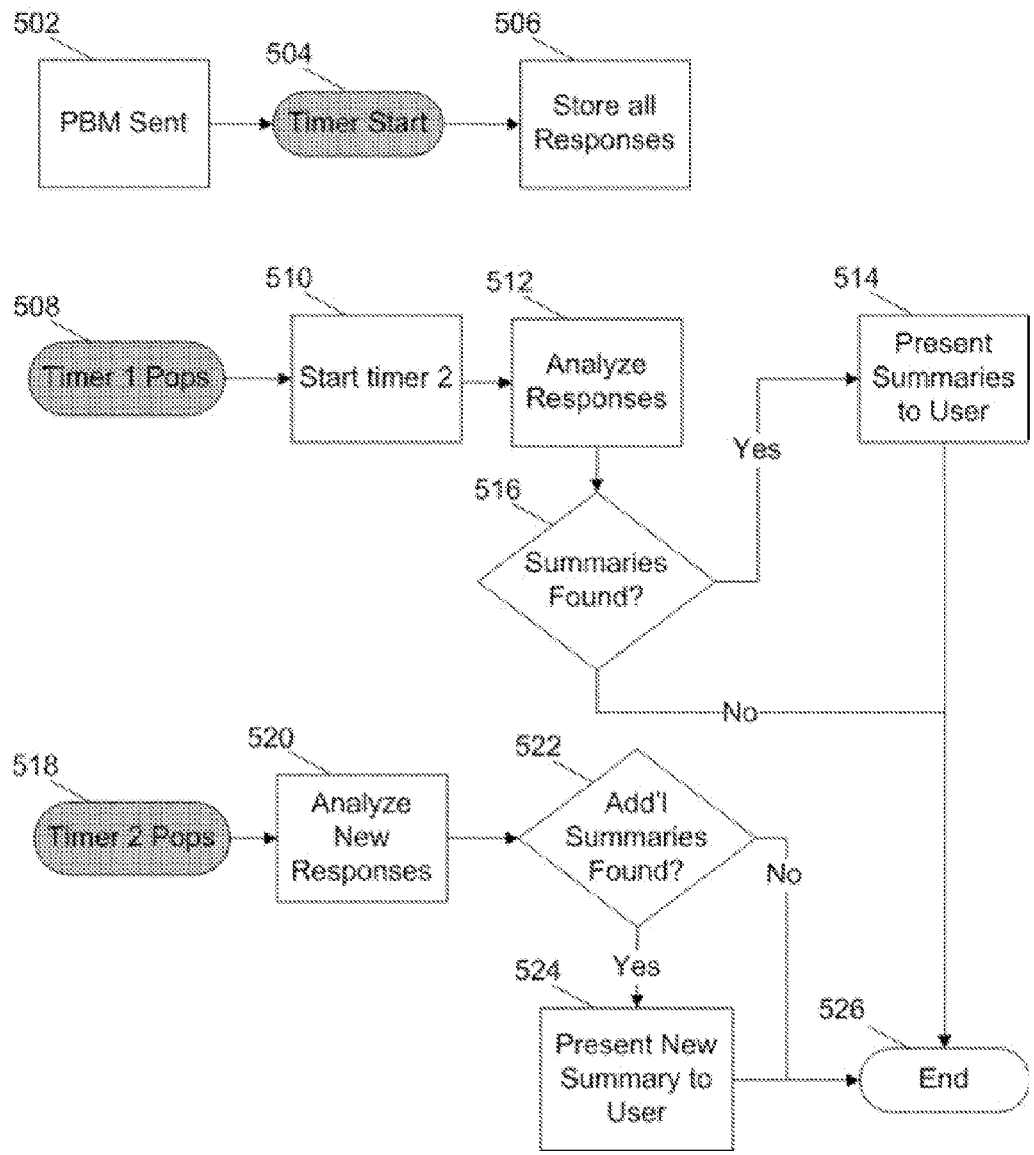
FIG. 9 illustrates another example flow diagram of a user message transfer, according to example embodiments.

FIG. 9 illustrates a flowchart of a PBM response analysis. Referring to FIG. 9, a flowchart is illustrated of a process used to analyze the responses to a PBM. The PBM is sent by the application 502 and responsive to sending the PBM a timer may be triggered to begin counting to a first time threshold 504. The application stores all of the responses from the recipients of the PBM 506. When the timer expires 508, the application begins a second timer for a second analysis 510. The analysis of the responses then begins 512. After analysis of the responses is completed, a check is performed to determine if any relevant summary data was determined 516. If summary data is not available to present to the user, the application displays a window to the user indicating that no relevant questions have been encountered and the process end 526. If relevant summary data has been found, the application presents the summaries to the user 514, and the process then ends 526.

The second timer expires 518 and the responses are again analyzed 520. A check is made to determine if the new analysis of the received responses is different from the original analysis 522. If there is no difference in the analysis, then the process ends 526. If a new summary message results from the additional analysis, the application displays a window to the user indicating the new summary information 524, and then the process ends 526. The user at this point has the option to respond with another PBM by answering the questions received.

The system uses an algorithm to analyze each of the responses to the PBM. This algorithm is used once the timer 1 expires 508, as well as when timer 2 expires 518. When analyzing the responses, the system first parses the responses to determine the nature of the response. Each of the responses is stored in the system in an internal database or at a remote storage server. For example purposes in the following algorithms, the individual responses from the recipients of the PBM are labeled A, B, C, D and E. In the analysis of the responses, each of the responses is diagnosed individually. In one example, the outcome of the analysis must be the same in order for a single response to be sent to the user. For example, IF (A=B=C=D=E) THEN (transmit a single response to the user). For this expression, each of the responses led the system to determine that the nature of the responses was equal and as a result no further action is necessary. In an alternative embodiment of the present application, any combination of the responses can be utilized for analysis, and the most appropriate response can be determined by the predetermined combination of the individual analysis.

In another example, each of the responses is analyzed individually and the outcome of the responses must be substantially equal in order for the analysis to be complete. IF (A=~B=~C=~D=~E) THEN (transmit a single response to the user). For this expression, the analysis of each of the responses led the system to determine that responses were substantially equal (e.g., substantial word overlap, substantial subject matter overlap, etc.). In this example, even if the responses' are not exactly equal, the nature of the responses is similar. In another embodiment of the present application, if there exists three similar or equal responses out of the 5 responses, then the analysis is deemed complete. IF (at least 3 or more of the 5 inputs are same or similar) THEN (analysis is complete). In another example, if the responses are analyzed together, the outcome must be substantially equal in order for the analysis to be complete. For example, IF (A~=B) OR (C~=D|E) THEN (analysis is complete) or IF (A~=D) OR (C|B~=E) Then (analysis is complete). Continuing this logic, taking any two of the inputs and comparing the results together would result in the same analysis.

In one example, let us assume that a broadcast message was sent out to all recipients with the text: "I'm wondering if the medication Hydrocodone may interact cohesively with regular aspirin." There were seven recipients that responded to the broadcast message with the following content: 1. "It should not have an interaction?" 2. "Not if you are taking under 30 mg of aspirin." 3. "How much Hydrocodone are you taking in a 24-hour period?" 4. "It should not", 5. "No." 6. "If regular dosages, there should not be an interaction." 7. "No". In The application, a determination is performed through analysis of the incoming responses that the most appropriate response to present to the user is: "No interaction". This is presented to the user via the application. This functionality permits the user to avoid reading each of the recipient's responses, but also gives the user the confidence that the most appropriate response was sent according to the majority of the responses received from the initial broadcast message.

Some example embodiments of the instant application include medicine related medical professionals, for example pharmacists, are able to provide new items of medical interest relating to the medicine that a user of the system may be taking. These submissions are known internally as awareness flags that are presented to the users of the system to keep them abreast of recent findings in the medical community. Also, entities in the network are able to submit updates to the system. The system notifies the affected users making them aware of present changes in the availability of medication and the possible side effects of medication. User's may be configured to receive a notification at a pre-determined time and may request additional data to help determine the side effect of a particular medication.

Public Broadcast Messages (PBMs) are sent by the user to entities in the system. The PBM changes according to the relationship of the recipient/receiver to the initiator/transmitter. For example, the closer the relationship of the transmitter and the receiver, the more detailed information will be provided in the message. The receivers that are not as close will receive only the original SMS text message. Responses to the PBM are received by the system and analyzed for duplication. The summary message of all of the received responses is sent to the initial user, permitting the user to receive a response to the PBM.

Figure 10:
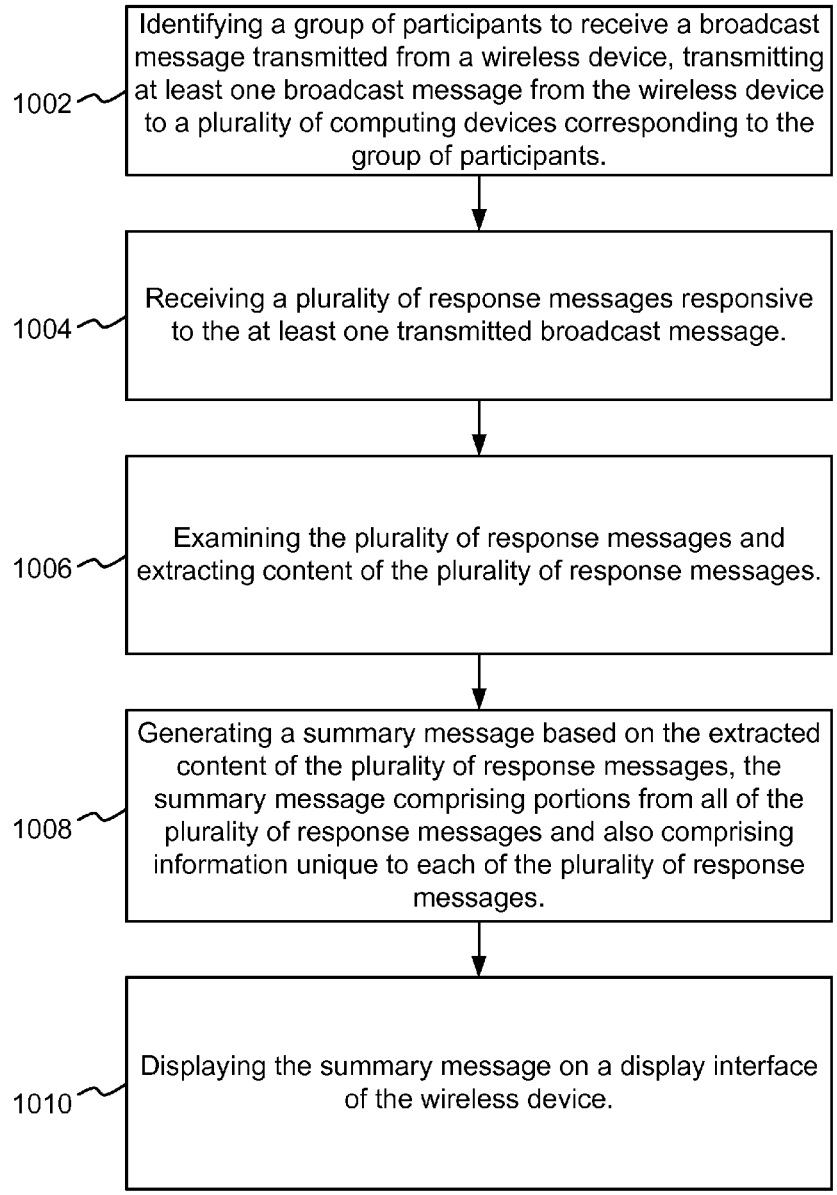
FIG. 10 illustrates another example flow diagram of an example method of operation, according to example embodiments.

FIG. 10 illustrates an example method of operation. Referring to FIG. 10, the method provides identifying a group of participants to receive a broadcast message transmitted from a wireless device and transmitting at least one broadcast message from the wireless device to a plurality of computing devices corresponding to the group of participants, at operation 1002. The method also include receiving a plurality of response messages responsive to the at least one transmitted broadcast message at operation 1004. The method also includes examining the plurality of response messages and extracting content of the plurality of response messages at operation 1006 and generating a summary message based on the extracted content of the plurality of response messages, the summary message including portions from all of the plurality of response messages and also comprising information unique to each of the plurality of response messages at operation 1008, and displaying the summary message on a display interface of the wireless device at operation 1010.

Figure 11:
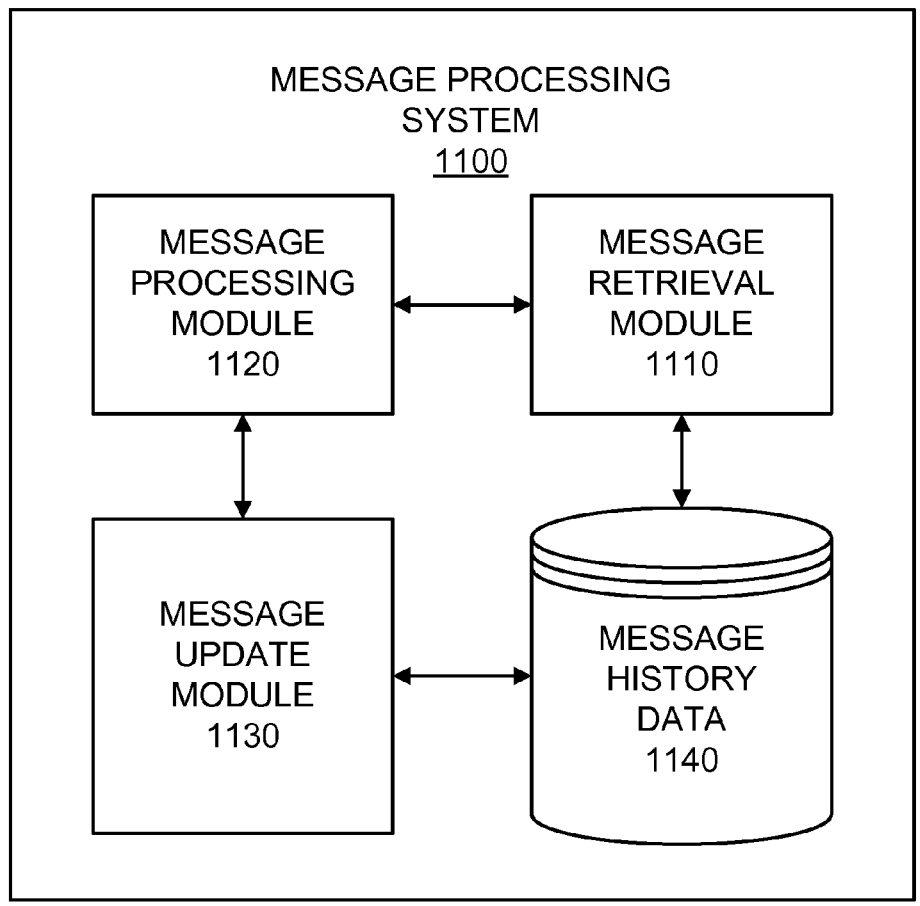
FIG. 11 illustrates an example system configuration according to example embodiments.

FIG. 11 illustrates an example system configured to perform one or more procedures or methods in accordance with example embodiments. Referring to FIG. 11, the message processing system 1100 includes message history data 1140 that may be retrieved and used to process new messages based on certain information known and stored in memory. According to one example method of operation, the system may identify a group of participants to receive a broadcast message transmitted from a wireless device, the participants may be based on known messages sent previously and stored in the history data 1140 or may be retrieved from a user list of known contacts. The message retrieval module 1110 may retrieve the stored history data 1140 and automatically establish a first tier of participants among the group of participants and designate at least one participant of the group of participants as part of only the first tier of participants. The retrieval module 1110 may also automatically establish at least one additional tier of participants among the group of participants and designate at least one additional participant of the group of participants as part of only the second tier of participants. The message processing module 1120 may transmit at least one broadcast message to a plurality of computing devices corresponding to the group of participants, the at least one broadcast message is transmitted to both the first tier of participants and the at least one additional tier of participants depending on the preconfigured tier information. The system may also transmit additional data to at least one member of the group of participants based on predefined relationship data identifying a relationship between the at least one member of the group of participants and a user of the wireless device. The additional data may only be transmitted to the first tier of participants. Changes to the recipients list, tier members, etc., may also be automatically generated and prepared for subsequent message broadcasting via the update module 1130.

The at least one broadcast message may be sent via at least one of a short message service (SMS) format, a video format, an audio format, and wherein the plurality of computing devices comprise at least one of a smartphone, cell phone, tablet computing device, personal computer, and a laptop computer. Each member of the group of participants are configured to receive the at least one broadcast message according to a predefined delivery preference specified for each participant of the group, such as SMS, email, voice message, telephone call, etc. The settings for each member may be identified and derived from previous message transmissions.

The at least one broadcast message is a first data type and the additional data is a second data type that is different from the first data type. For example, one message may be text, and the next is an image, video, audio or a combination thereof. The system may then identify a message transfer history of the wireless device based on a number of messages transferred from the mobile device to each of the participants in the group of participants and also identify a first group of participants having been sent more messages than a remaining group of participants that have been sent fewer messages than the first group of participants based on the message transfer history. The system may then designate the first group of participants as part of the first tier of participants and designate the second group of participants as part of the second tier of participants. The first tier of participants are configured to receive data messages corresponding to at least two of text data, video data, audio data, and the second tier of participants are configured to only receive one of text data, video data and audio data. The first tier may be a closer or more privileged group of members than the second group.

Another example method of operation may include the system identifying a group of participants to receive a broadcast message transmitted from a wireless device and transmitting at least one broadcast message from the wireless device to a plurality of computing devices corresponding to the group of participants. In response, a plurality of response messages may be received responsive to the at least one transmitted broadcast message, which are then examined so content of the plurality of response messages may be extracted and processed prior to delivering the information to the original user. In one example, message retrieval module 1110 may retrieve the messages and the processing module 1120 may process the messages to generate a summary message based on the extracted content of the plurality of response messages, the summary message may include portions from all of the plurality of response messages and also information unique to each of the plurality of response messages. For example, a noun and/or verb from each message may be included in a single summary message, the noun or verb may be extracted via a parsing operation. Those keywords, nouns, verbs, etc., that are the same in each message may be included in the summary only one time. The summary message may be displayed on a display interface of the wireless device.

The at least one broadcast message may be sent via at least one of a short message service (SMS) format, a video format, an audio format, and the plurality of computing devices may include at least one of a smartphone, cell phone, tablet computing device, personal computer, and a laptop computer. The examining of the plurality of response messages and the extracting content of the plurality of response messages may be performed after a predetermined time threshold has expired. The predetermined time threshold may be 10 seconds, 20 seconds, 30 seconds and 60 seconds or longer. The method may then perform reexamining the plurality of response messages and extracting additional content of the plurality of response messages different from previously extracted content. The method may also perform generating another summary message based on the extracted additional content of the plurality of response messages, and displaying the new summary message with at least a portion of the extracted additional content on a display interface of the wireless device if the extracted additional content was not part of the summary message. The new summary message may be based on new response messages received since the initial group of response messages. For example, five response messages may be received in a 60 second period and processed to create one summary message. 60 seconds later than the initial seconds another four messages may be processed to create a second summary message. The content of the new summary message may first be filtered based on the content of the first summary message so only new information in the second group of four messages is processed to be part of the new summary message. This ensures that only new information is forwarded to the user each time a summary message is generated. The reexamining the plurality of response messages may be performed by examining at least one additional response message that was not previously received and examined at a time of the first examining procedure. Also, the reexamining of the plurality of response messages and the extracting additional content of the plurality of response messages is performed after a predetermined second time threshold has expired that is a later time than the first time threshold (e.g., 1 examination per minute).

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example FIG. 12 illustrates an example network element 1200, which may represent any of the above-described network components, etc.

Figure 12:
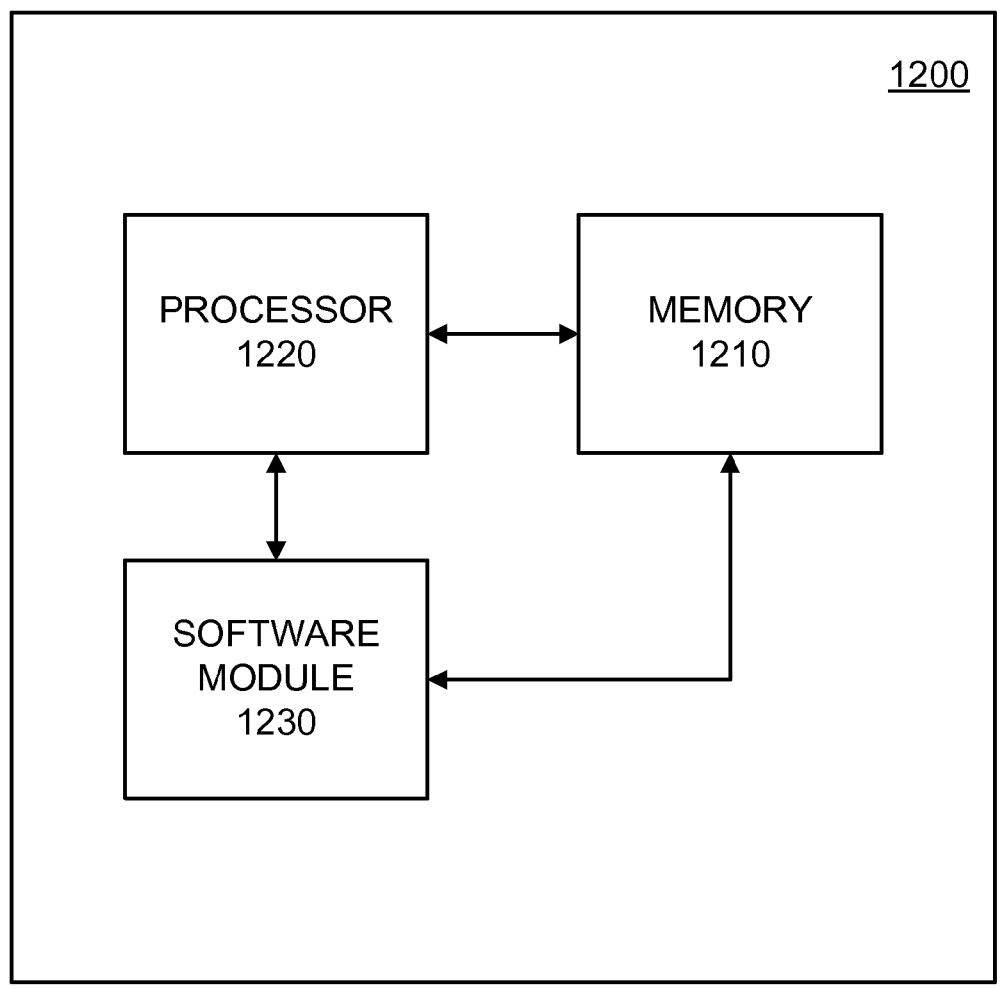
FIG. 12 illustrates an example network entity device configured to store instructions, software, and corresponding hardware for executing the same, according to example embodiments.

As illustrated in FIG. 12, a memory 1210 and a processor 1220 may be discrete components of the network entity 1200 that are used to execute an application or set of operations. The application may be coded in software in a computer language understood by the processor 1220, and stored in a computer readable medium, such as, the memory 1210. The computer readable medium may be a non-transitory computer readable medium that includes tangible hardware components in addition to software stored in memory. Furthermore, a software module 1230 may be another discrete entity that is part of the network entity 1200, and which contains software instructions that may be executed by the processor 1220. In addition to the above noted components of the network entity 1200, the network entity 1200 may also have a transmitter and receiver pair configured to receive and transmit communication signals (not shown).

Although an exemplary embodiment of the system, method, and computer readable medium of the present invention has been illustrated in the accompanied drawings and described in the foregoing detailed description, it will be understood that the invention is not limited to the embodiments disclosed, but is capable of numerous rearrangements, modifications, and substitutions without departing from the spirit or scope of the invention as set forth and defined by the following claims. For example, the capabilities of the systems can be performed by one or more of the modules or components described herein or in a distributed architecture. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:
1. A method comprising:
identifying a group of participants to receive a broadcast message transmitted from a wireless device, wherein the group comprises at least one of selected medical doctors, pharmacists, home remedy specialists, and drug manufacturer personnel with expertise in a first ailment/diagnosis;
transmitting at least one broadcast message from the wireless device to a plurality of computing devices corresponding to the group of participants;
receiving a plurality of response messages responsive to the at least one transmitted broadcast message;

examining the plurality of response messages and extracting content of the plurality of response messages;

generating a summary message based on the extracted content of the plurality of response messages, the summary message comprising portions from all of the plurality of response messages and also comprising information unique to each of the plurality of response messages; and displaying the summary message on a display interface of the wireless device, wherein the summary message is in reference to at least one of medications and remedies directed to the first ailment/diagnosis, wherein the group is further segmented into recipient tiers based on closeness of relationship of participants with a sender of the broadcast message and wherein the tiers accordingly receive the broadcast message with differing levels of pertinence and personalization reflecting closeness of relationship.

2. The method of claim 1, wherein the at least one broadcast message is sent via at least one of a short message service (SMS) format, a video format, an audio format, and wherein the plurality of computing devices comprise at least one of a smartphone, cell phone, tablet computing device, personal computer, and a laptop computer.

3. The method of claim 1, wherein the examining the plurality of response messages and the extracting content of the plurality of response messages is performed after a predetermined time threshold for receiving the plurality of response messages has expired.

4. The method of claim 3, wherein the predetermined time threshold is at least one of 10 seconds, 20 seconds, 30 seconds and 60 seconds.

5. The method of claim 3, further comprising:

reexamining the plurality of response messages and extracting additional content of the plurality of response messages different from previously extracted content;

generating another summary message based on the extracted additional content of the plurality of response messages; and displaying the another summary message with at least a portion of the extracted additional content on a display interface of the wireless device if the extracted additional content was not part of the summary message.

6. The method of claim 5, wherein the reexamining the plurality of response messages further comprises examining at least one additional response message that was not previously received and examined at a time of the first examining procedure.

7. The method of claim 6, wherein the reexamining the plurality of response messages and the extracting additional content of the plurality of response messages is performed after a predetermined second time threshold has expired that is a later time than the first time threshold.

8. An apparatus comprising:

a processor configured to identify a group of participants to receive a broadcast message transmitted from a wireless device, wherein the group comprises at least one of selected medical doctors, pharmacists, home remedy specialists, and drug manufacturer personnel with expertise in a first ailment/diagnosis;

a transmitter configured to transmit at least one broadcast message to a plurality of computing devices corresponding to the group of participants;

a receiver configured to receive a plurality of response messages responsive to the at least one transmitted broadcast message;

wherein the processor is further configured to examine the plurality of response messages and extracting content of the plurality of response messages, generate a summary message based on the extracted content of the plurality of response messages, the summary message comprising portions from all of the plurality of response messages and also comprising information unique to each of the plurality of response messages, wherein the summary message is in reference to at least one of medications and remedies directed to the first ailment/diagnosis; and a display configured to display the summary message, wherein the group is further segmented into recipient tiers based on closeness of relationship of participants with a sender of the broadcast message and wherein the tiers accordingly receive the broadcast message with differing levels of pertinence and personalization reflecting closeness of relationship.

9. The apparatus of claim 8, wherein the at least one broadcast message is sent via at least one of a short message service (SMS) format, a video format, an audio format, and wherein the plurality of computing devices comprise at least one of a smartphone, cell phone, tablet computing device, personal computer, and a laptop computer.

10. The apparatus of claim 8, wherein the processor is configured to examine the plurality of response messages and the extract content of the plurality of response messages after a predetermined time threshold for receiving the plurality of response messages has expired.

11. The apparatus of claim 10, wherein the predetermined time threshold is at least one of 10 seconds, 20 seconds, 30 seconds and 60 seconds.

12. The apparatus of claim 10, wherein the processor is further configured to reexamine the plurality of response messages and extract additional content of the plurality of response messages different from previously extracted content, generate another summary message based on the extracted additional content of the plurality of response messages, and display the another summary message with at least a portion of the extracted additional content on a display interface of the wireless device if the extracted additional content was not part of the summary message.

13. The apparatus of claim 12, wherein the processor is configured to reexamine the plurality of response messages by examining at least one additional response message that was not previously received and examined at a time of the first examination.

14. The apparatus of claim 12, wherein the processor is configured to reexamine the plurality of response messages and extract additional content of the plurality of response messages after a predetermined second time threshold has expired that is a later time than the first time threshold.

15. A non-transitory computer readable storage medium configured to store instructions that when executed cause a processor to perform:

identifying a group of participants to receive a broadcast message transmitted from a wireless device, wherein the group comprises at least one of selected medical doctors, pharmacists, home remedy specialists, and drug manufacturer personnel with expertise in a first ailment/diagnosis;

transmitting at least one broadcast message from the wireless device to a plurality of computing devices corresponding to the group of participants;

receiving a plurality of response messages responsive to the at least one transmitted broadcast message;

examining the plurality of response messages and extracting content of the plurality of response messages;

generating a summary message based on the extracted content of the plurality of response messages, the summary message comprising portions from all of the plurality of response messages and also comprising information unique to each of the plurality of response messages, wherein the summary message is in reference to at least one of medications and remedies directed to the first ailment/diagnosis; and displaying the summary message on a display interface of the wireless device, wherein the group is further segmented into recipient tiers based on closeness of relationship of participants with a sender of the broadcast message and wherein the tiers accordingly receive the broadcast message with differing levels of pertinence and personalization reflecting closeness of relationship.

16. The non-transitory computer readable storage medium configured of claim 15, wherein the at least one broadcast message is sent via at least one of a short message service (SMS) format, a video format, an audio format, and wherein the plurality of computing devices comprise at least one of a smartphone, cell phone, tablet computing device, personal computer, and a laptop computer.

17. The non-transitory computer readable storage medium configured of claim 15, wherein the examining the plurality of response messages and the extracting content of the plurality of response messages is performed after a predetermined time threshold for receiving the plurality of response messages has expired.

18. The non-transitory computer readable storage medium configured of claim 17, wherein the predetermined time threshold is at least one of 10 seconds, 20 seconds, 30 seconds and 60 seconds.

19. The non-transitory computer readable storage medium configured of claim 17, wherein the processor is further configured to perform:

reexamining the plurality of response messages and extracting additional content of the plurality of response messages different from previously extracted content;

generating another summary message based on the extracted additional content of the plurality of response messages; and displaying the another summary message with at least a portion of the extracted additional content on a display interface of the wireless device if the extracted additional content was not part of the summary message.

20. The non-transitory computer readable storage medium configured of claim 19, wherein the reexamining the plurality of response messages further comprises examining at least one additional response message that was not previously received and examined at a time of the first examining procedure, and wherein the reexamining the plurality of response messages and the extracting additional content of the plurality of response messages is performed after a predetermined second time threshold has expired that is a later time than the first time threshold.

* * * * *